United States Patent [19]

Issenmann

[11] Patent Number: 5,090,256
[45] Date of Patent: Feb. 25, 1992

[54] METHOD AND APPARATUS FOR SAMPLING THE GASEOUS CONTENT OF A LIQUID

[75] Inventor: Olivier Issenmann, Neuilly Sur Seine, France

[73] Assignee: Geoservices, Le Blanc Mesnil, France

[21] Appl. No.: 441,546

[22] Filed: Nov. 27, 1989

[30] Foreign Application Priority Data

Apr. 26, 1989 [FR] France .................. 89 05518

[51] Int. Cl.⁵ .............................................. G01N 1/00
[52] U.S. Cl. .............................. 73/863.23; 73/863.21
[58] Field of Search ............... 73/153, 863.23, 863.24, 73/864.34, 864.81, 863.21; 175/40, 50, 48, 66, 206; 166/250, 264, 265

[56] References Cited

U.S. PATENT DOCUMENTS

| | | | |
|---|---|---|---|
| 2,700,897 | 2/1955 | Arps | 175/50 |
| 2,704,658 | 3/1955 | Gordon | 73/153 |
| 2,923,151 | 2/1960 | Engle et al. | 175/206 |
| 3,039,309 | 6/1962 | Vesper et al. | 73/863.24 |
| 3,759,087 | 9/1973 | Iwao et al. | 73/863.12 |
| 4,319,482 | 3/1982 | Bunner | 73/153 |
| 4,546,640 | 10/1985 | Stone et al. | 73/153 |
| 4,635,735 | 1/1987 | Crownover | 175/50 |
| 4,699,886 | 10/1987 | Lelong | 73/863.12 |
| 4,739,655 | 4/1988 | Greer et al. | 73/153 |
| 4,765,182 | 8/1988 | Boone | 73/153 |
| 4,836,917 | 6/1989 | Tomita et al. | 210/104 |
| 4,887,464 | 12/1989 | Tannenbaum et al. | 73/153 |

*Primary Examiner*—Robert Raevis
*Attorney, Agent, or Firm*—Wenderoth, Lind & Ponack

[57] ABSTRACT

A method and apparatus for sampling the gaseous content of a liquid laden with solids initially involves sampling the liquid as close as possible to the source of the liquid. A strainer housing having a strainer plate for filtering out debris in the liquid is connected to a suction pump for sucking the liquid into the housing and to the pump. The pump delivers the sampled liquid to a degassing device mounted on a frame with the pump. The degassing device agitates the liquid to liberate gases suspended therein. The gases are then collected from the degassing device so that the gases may be analyzed. A motor mechanism on the frame drives the pump, a rotating agitator in the degassing device and a rotating scraper on the exterior of the strainer plate simultaneously. This method and apparatus are particularly applicable to the sampling of drilling mud from an oil well exploration site for purposes of analyzing the hydrocarbon content of the drilling mud.

22 Claims, 7 Drawing Sheets

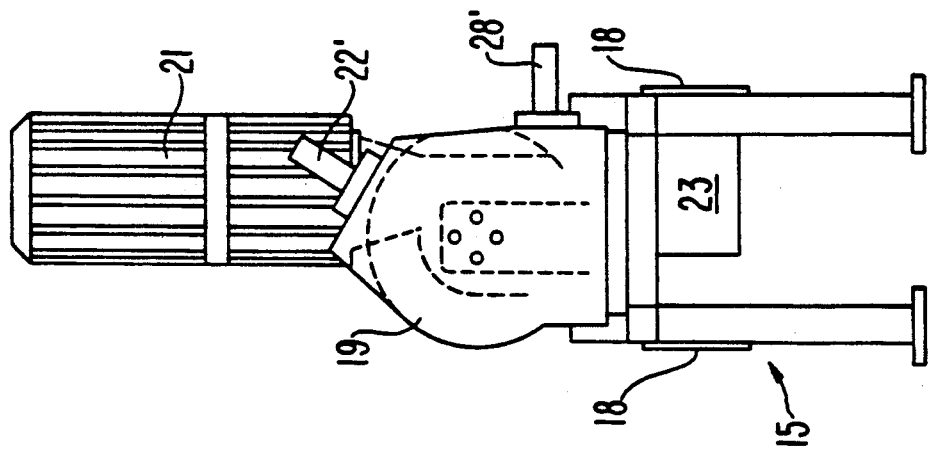
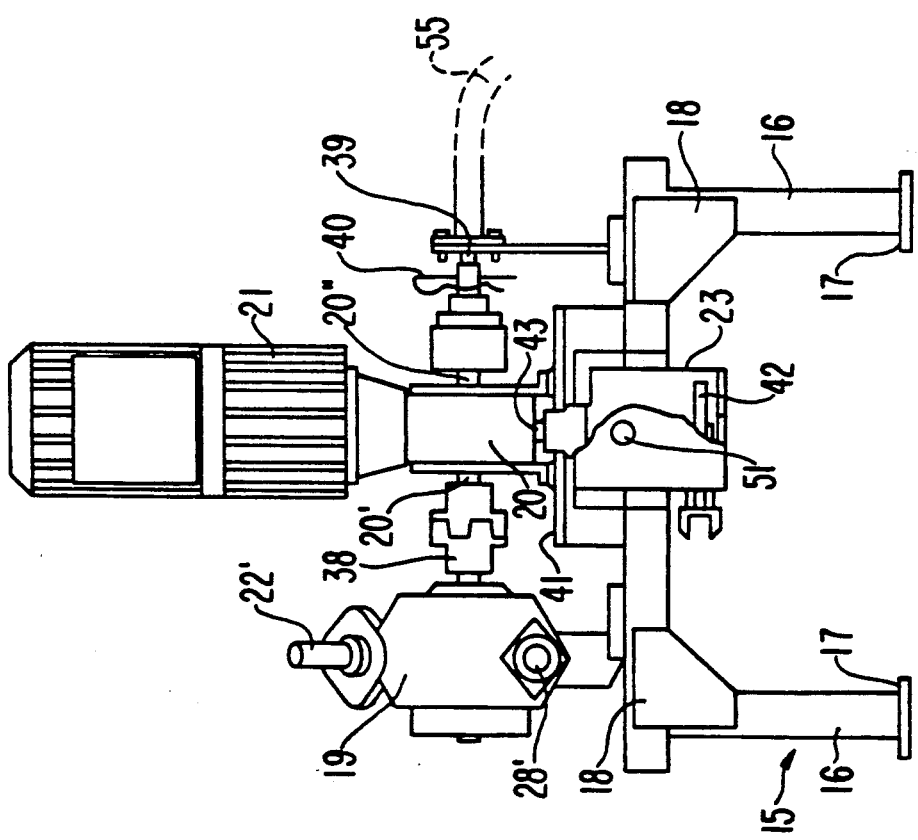

METHOD AND APPARATUS FOR SAMPLING THE GASEOUS CONTENT OF A LIQUID

BACKGROUND OF THE INVENTION (1) Field of the Invention

The present invention relates to a method and apparatus for continuously and evenly drawing off samples of gases which are contained in a liquid laden with solids. More particularly, the present invention relates to a method and apparatus for obtaining samples of gases contained in drilling mud from an oil well or oil exploration site.

(2) State of the Prior Art

A normal practice at oil exploration and drilling sites is to use a special fluid, termed "drilling mud," to circulate in a drilling well. This fluid, whether the fluid is water or oil based, brings to the well surface rocky debris produced by the drilling of the well by the drill bit. Gaseous products originally contained in the drilled rocks are held in suspension in the fluid bringing the rocky debris to the surface. The gaseous products suspended in the fluid may be composed of hydrocarbons, which are indications that oil or gas deposits exist at the drilling site.

It is conventional to use the special drilling fluid or drilling mud to bring to the surface rocky debris and traces of hydrocarbons so that samples of the hydrocarbons may be extracted and analyzed. By this analysis, the geologic succession of strata penetrated by the drill can be determined and the existing opportunities for mining gas or oil deposits can be deduced. This practice is termed "mud logging."

With present methods, rocky debris is separated out of the fluid by filtration on vibrating screens. The gas, i.e. hydrocarbon, samples are collected in a gas trap. This gas trap normally comprises a chamber open at its base and immersed in the flow of mud emerging from the well. The occluded gases in the mud flow rise in the chamber. The chamber is fitted with an overflow for discharge of the mud in the chamber. The gases are suctioned through the chamber by the centrifugal effect of an agitator disposed in the chamber, and are then released by a regulating nozzle into a conventional scanning system.

FIG. 1 schematically illustrates a conventional mud degassing apparatus as described above. This device has a chamber 1, the chamber 1 being unitary and one piece with a support (not shown). The chamber is positioned on the upper portion of a tank 2 into which drilling mud is poured through a feed tube or chute 3. The drilling mud fills the tank 2 up to a level indicated by numeral 4 and is discharged by an overflow device 5 onto a vibrating screen 6 positioned above an outlet 7. The chamber 1, which may be cylindrical, has an inner shaped collar 8 at its lower end defining a circular opening 9. An agitator bar 11 is carried by a shaft 12 of a drive motor 13 and is positioned above the circular opening 9. A mud drainage nozzle 10 is positioned on the side of the cylindrical chamber above the agitator bar 11. The degassing chamber 1 has on its upper end a nozzle 14 for evacuating the gases collected inside the degassing chamber.

With this conventional device, it is impossible to know the precise volume of mud subjected to degassing over a given period of time. Nor is it possible to determine any definite relationship between the volume of degassed mud and the volume of gas released, in view of the heterogeneous nature of the mud in the tank and the relatively long path the mud has traveled from the outlet of the drilling well, the gas content of the mud being at least partially and unevenly lost before the mud discharges gas into the chamber 1.

As has been indicated above, in this system the flow rate of the mud, which may be approximately 58 liters per minute, is not precisely known. The flow rate of the mud varies as a function of the density and viscosity of the mud, and especially as a function of the changes in the level of the mud in the tank in which the degassing chamber is immersed. Furthermore, the exact proportion of gases which are extracted from the mud is unknown. Also, the need to have a plane surface of mud available (see FIG. 1) requires the placement of the gas trap at a fairly considerable distance from the outlet of the drilling well, normally over the feed reservoir of the vibrating screens. The mud reaching this site thus has travelled some distance in the open air and has partially discharged its gases into the air. Flow turbulence of the mud in the conduit or chute feeding into the vibrating screens further assists the discharge of the gas into the air. Furthermore, conventional devices of this type can only provide approximate or some times even false data, because some heavier hydrocarbons can easily avoid analysis and be directly lost or underestimated.

Accordingly, measurements taken with the above described apparatus cannot be quantified, and are not comparable from one point in time to another nor from one drill site to another, nor even from one apparatus to another. Although the gaseous mixture which is obtained is measured and analyzed with precision, there is no known stable relationship between the results obtained and the quantities which are actually present in the mud. Such a relationship would enable the deduction, by simple calculation, of the proportions and quantities of hydrocarbons contained in the respective geologic layers.

The exact measurement and analysis of gases conveyed by drilling mud are, therefore, of extreme importance in carrying out mud logging procedures. Furthermore, mud logging is the only means of gaining direct knowledge of the presence of usable hydrocarbons in the subterranean layers through which the drill bit penetrates, as well as the relative proportions of the various hydrocarbons detected, i.e. methane, ethane, propane, butane and pentane. It is the only manner in which an accurate reading can be obtained.

Although various devices have been used to determine the quantities of gases in drilling mud, none of these devices provides a continuous and automatic indication of the quantities of occluded gases in a given volume of mud corresponding to an easily identifiable geological layer.

SUMMARY OF THE INVENTION

The objects of the present invention are, accordingly, to provide a method and apparatus for sampling the gaseous content of a liquid laden with solids which provide continuous and automatic indications of the quantities of gases in a given volume of a liquid.

The objects of the present invention are accomplished by providing a method of continuously sampling the gas content of a liquid laden with solids. The method includes continuously drawing off a predetermined quantity of the sample of the liquid over a predetermined period of time. The predetermined quantity of liquid is transferred to a degassing chamber, which chamber has a constant predetermined volume. The predetermined quantity of liquid in the chamber is degassed over a certain period of time, and the gas released from the predetermined quantity of liquid is drawn off and transported to an analyzing and measuring device.

The above described method of the present invention is particularly applicable to determining the types and quantities of gases found in drilling mud at an oil well exploration site. The drilling mud of the oil well is sampled and degassed to obtain and analyze hydrocarbon gases which were occluded in the mud of the oil well. The sample liquid or drilling mud should be drawn off continuously and as close as possible to the well for the best results. The analyzing and measuring device is conventional, and may be a flame ionization measuring device.

The objects of the present invention are further accomplished by the provision of an apparatus for sampling the gaseous content of a liquid laden with solids. As with the above method, the apparatus of the present invention is especially applicable to the sampling of gaseous hydrocarbons suspended in drilling mud obtained from an oil exploration well.

The apparatus of the present invention for sampling the gaseous content of a liquid laden with solids has an arrangement for collecting sample liquid from a stream of the liquid and delivering substantially all of the sample liquid to a degassing device. The sample gas obtained in the degassing device is delivered from the degassing device to an analyzing device.

The arrangement for collecting and delivering the sample liquid of the present invention is characterized by a pump having an input and an output connection, a flexible suction tube connected to the input connection of the pump and an output connection fluidly connected to the degassing device. Furthermore, a device is provided for driving the pump. Preferably, the device for driving the pump is a motor drivingly connected to the pump.

In a preferred form of the present invention, the flexible suction tube has a suction strainer at its suction end. More specifically, the suction strainer includes a hollow strainer housing connected to the flexible suction tube, a strainer plate on a suction side of the hollow strainer housing and a device for continuously scraping the exterior side of the strainer plate when the pump is suctioning sample fluid through the flexible suction tube and the hollow strainer housing.

Preferably, the device for continuously scraping the exterior of the strainer plate is a rotating scraper rotatably mounted on the exterior of the strainer plate. A rotary driving mechanism is connected to the rotating scraper and is drivably connected to the device which drives the pump.

In a further preferred form of the invention, the hollow strainer housing is cylindrical on its interior, the rotary driving mechanism extends through the housing, and a radial agitator blade is mounted on the rotary driving mechanism inside the strainer housing so as to rotate with the rotating scraper and agitate sample liquid inside the housing. Preferably, the strainer plate and at least a portion of the scraper are made of the same material, this material having a hardness sufficient to resist abrasion by any solids in the sample liquid. This material may be, for example, tungsten carbide. Furthermore, a capped nut and a spring can be disposed on the exterior of the hollow strainer housing for biasing the rotating scraper against the strainer plate.

Preferably, the rotary driving mechanism comprises a shaft which extends through the hollow strainer housing and is connected to the rotating scraper. A bowden wire is connected between the shaft and the device driving the pump to rotate the shaft, the rotating scraper, and the radial agitator blade.

A support frame may also be provided for supporting the entire device, the support frame having a support plate and a plurality of support legs connected thereto. The degassing device is connected to the underside of the support plate.

According to further preferred features of the present invention, the degassing device is a degassing container which has an inlet connection for receiving sample liquid therethrough, a rotary degassing agitator, and a discharge nozzle for discharging degassed sample liquid. A gas evacuation tube serves to conduct sample gas from the degassing device to the analyzing device. Preferably, the rotary degassing agitator is also driven by the motor or other device driving the pump and the rotary driving mechanism of the strainer housing. A lateral portion of the degassing container has the discharge nozzle thereon for discharging the degassed liquid from the container. The degassing container also has two radial deflectors disposed above the rotary agitator, an inner collar defining a circular opening in the container and a rotary disk between the motor and the rotary agitator. The radial deflectors are disposed below the inner collar. The inner collar defines an opening which has a diameter at most equal to the diameter of the rotary disk. In a further preferred feature of the degassing device, the degassing device may be removably mounted to the underside of the support plate. Furthermore, the degassing container may have a peripheral collar thereon for seating an O-ring seal for sealing contact with the support plate.

In accordance with the above described method of continuously sampling the gas contents of a liquid laden with solids, the apparatus of the present invention is positioned as close as possible to the source of the liquid to prevent the escape of gases therefrom. When used with an oil exploration well, the device is positioned as close as possible to the well outlet. The device thus allows continuous sampling of the gaseous content of the drilling mud, ensuring that properties of the gaseous hydrocarbons sampled correspond as closely as possible to the properties found at the well bottom. The device is thus capable of providing accurate and valuable information about the oil production site by analysis of these hydrocarbons.

BRIEF DESCRIPTION OF THE DRAWINGS

Further characteristics, features and advantages of the method and apparatus for sampling the gaseous content of a liquid laden with solids will become clear from the following detailed description of a preferred embodiment thereof, with reference to the accompanying drawings, wherein:

FIG. 3 is a partial schematic elevational view of the degassing and sampling device according to FIG. 2;

FIG. 4 is a schematic side view of the device of FIG. 3;

DESCRIPTION OF THE PREFERRED EMBODIMENT

Figure 1:
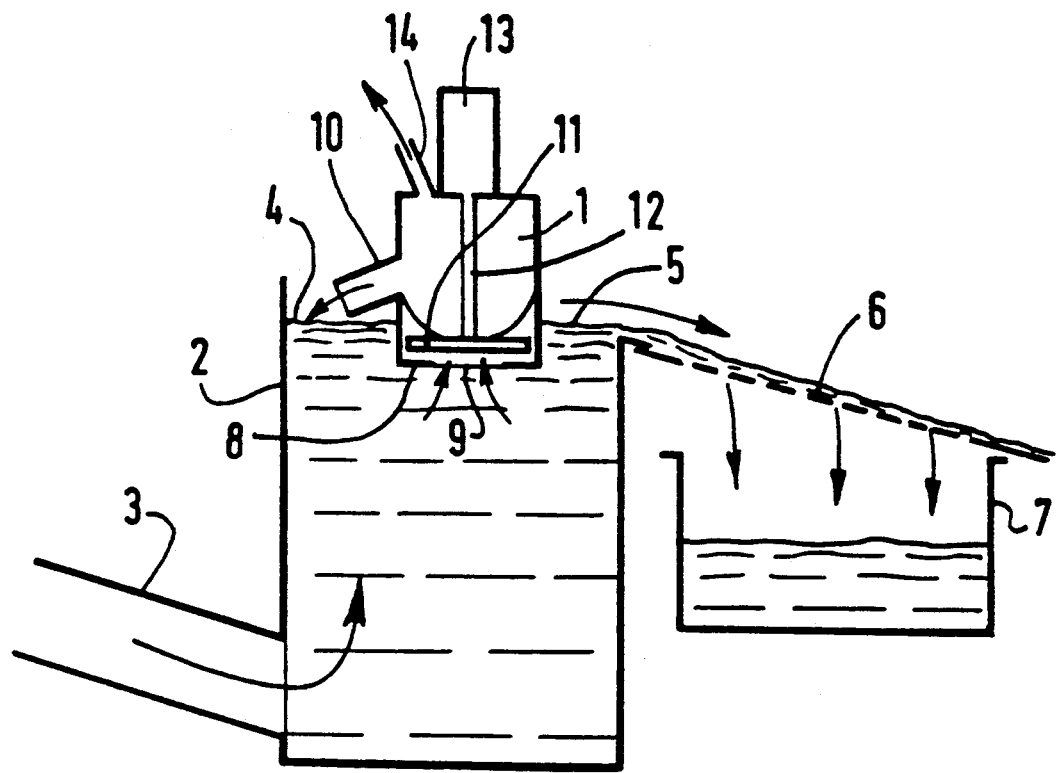
FIG. 1 is a schematic, elevational view of an axial cross-section of a conventional mud degassing device immersed in a mud receiving tank.
Figure 2:
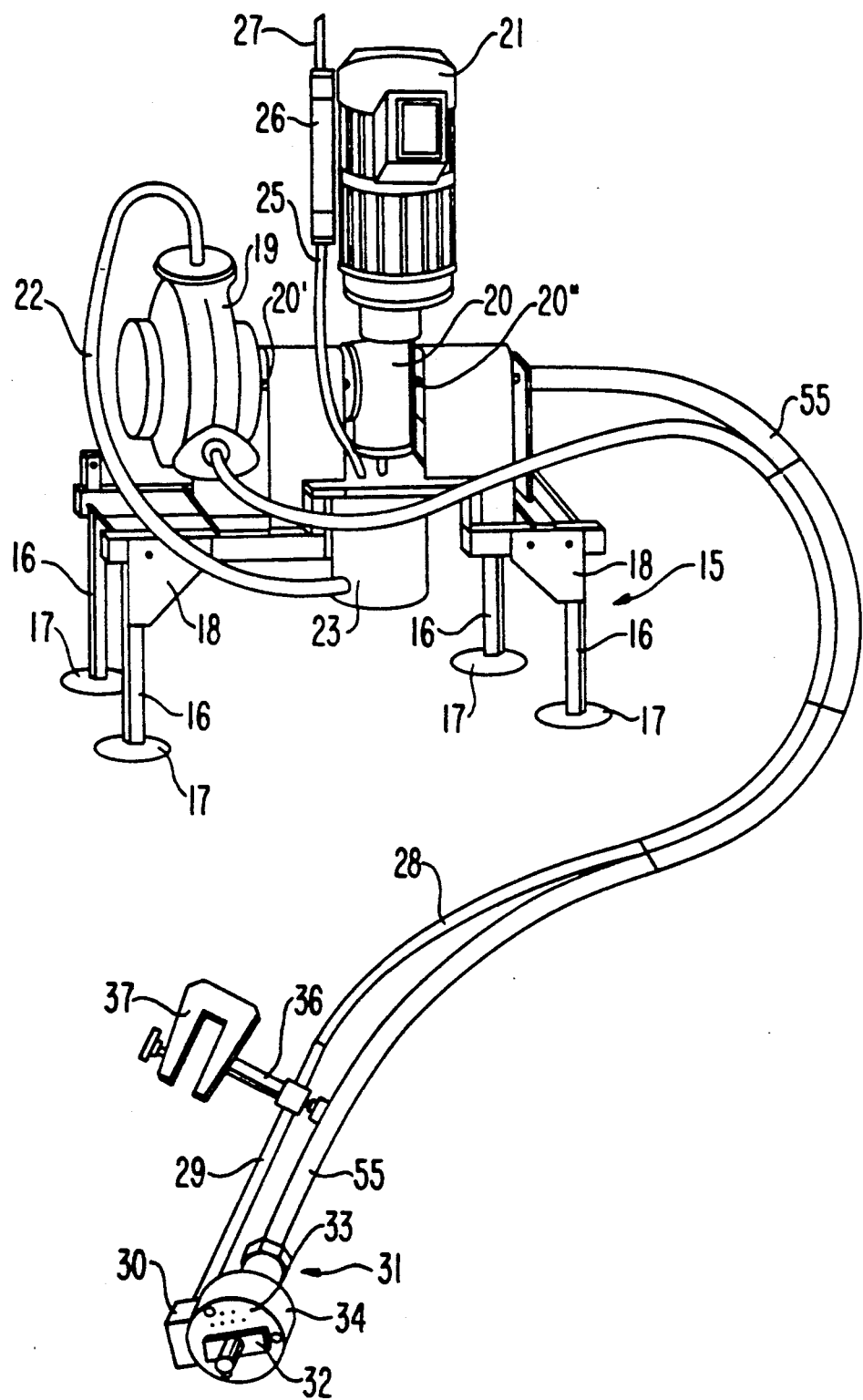
FIG. 2 is a schematic perspective view of a liquid degassing and sampling device according to the present invention.

An apparatus for sampling the gaseous content of a liquid laden with solids according to the present invention is illustrated in FIGS. 2–11. Initially noting FIG. 2, there is shown a support for the overall apparatus. The support may comprise a support frame 15 having four legs 16 fitted with support shoes 17. The legs 16 may be strengthened by stiffening plates 18. The apparatus, accordingly, is very portable and easily installed.

The apparatus basically comprises a degassing device shown at 23, an arrangement for collecting and delivering a liquid laden with solids to the degassing device for degassing the liquid and obtaining a gaseous sample thereof, and an arrangement for delivering the gas collected in the degassing device to an analyzing device. In accordance with the invention, the liquid laden with solids is obtained as close as possible to its source to prevent the escape therefrom of gases occluded therein. Furthermore, once the arrangement for collecting and delivering the liquid collects the liquid, the liquid is held out of contact with the atmosphere to prevent any further escape of gas.

The arrangement for collecting and delivering the liquid laden with solids to the degassing device 23 may comprise a rotary pump 19 having an input side and an output side. On the input side is connected a flexible suction tube 28 for collecting the liquid laden with solids. On the suction end of the tube 28 is connected a rigid tube 29, which is further connected to a collecting cavity 30. A strainer 31 having a cylindrical chamber therein is connected to the collecting cavity 30.

The output of the rotary pump 19 is connected, via a flexible tube 22, to an input nozzle of the degassing device 23. The degassing device 23 is a container for receiving the liquid laden with solids therein. A nozzle 24 (see FIG. 5) is connected to the degassing device 23, preferably on its upper portion. A flexible tube 25 is connected to the nozzle 24 for conveying gases released from the liquid inside the container of the degassing device 23 to a collecting tube 26 mounted thereto. The collecting tube 26, in turn, delivers the gases through a tube 27 to an analyzing device (not shown).

The rotary pump 19 is a constant flow generating type of pump, and is driven by a motor 21 mounted on the support frame 15. The motor 21 is connected to the rotary pump 19 by a reducing gear 20. Two outputs 20', 20" are on the reducing gear 20. The pump 19 is connected to the reducing gear 20 via the output 20'. Noting FIG. 3, a joint 38 is connected to a Cardan drive at output 20' of the reducing gear 20.

The degassing device 23 is preferably a container attached to a support plate 41. As can be seen especially from FIGS. 3–5, the degassing container is placed underneath the support plate 41. The liquid pumped by the pump 19 is fed to the degassing device at a lower portion of the container. Note particularly FIG. 5. Inside the container is an agitator bar 42, seen in FIGS. 5 and 6, the agitator bar 42 being driven by an output shaft 43 of the motor 21. The output shaft 43 passes through the reducing gear 20.

Figure 7:
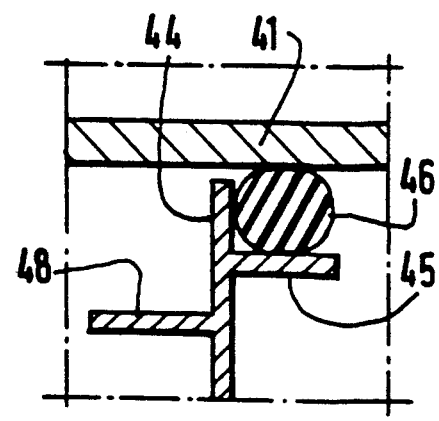
FIG. 7 is an enlarged, cross-sectional view of a detail indicated in broken lines in FIG. 5 illustrating the sealed connection of a degassing container of the device to a supporting plate.

The degassing device 23 is supported on the underside of the support plate 41 so as to be movable. The degassing device is held in place using clamping and traction devices (not shown) fastened to the support frame 15 and work positioning tabs (also not shown) pressing the degassing device 23 against the support plate 41. Noting FIG. 5 and the detail of FIG. 7, the container of the degassing device 23 has a peripheral flange or collar 45 on an upper portion 44 thereof. An O-ring seal 46, made of an elastic material, rests on the flange 45, as seen in FIG. 7. The O-ring seal is pressed against the underside of support plate 41 to seal the container of the degassing device 23.

Figure 5:
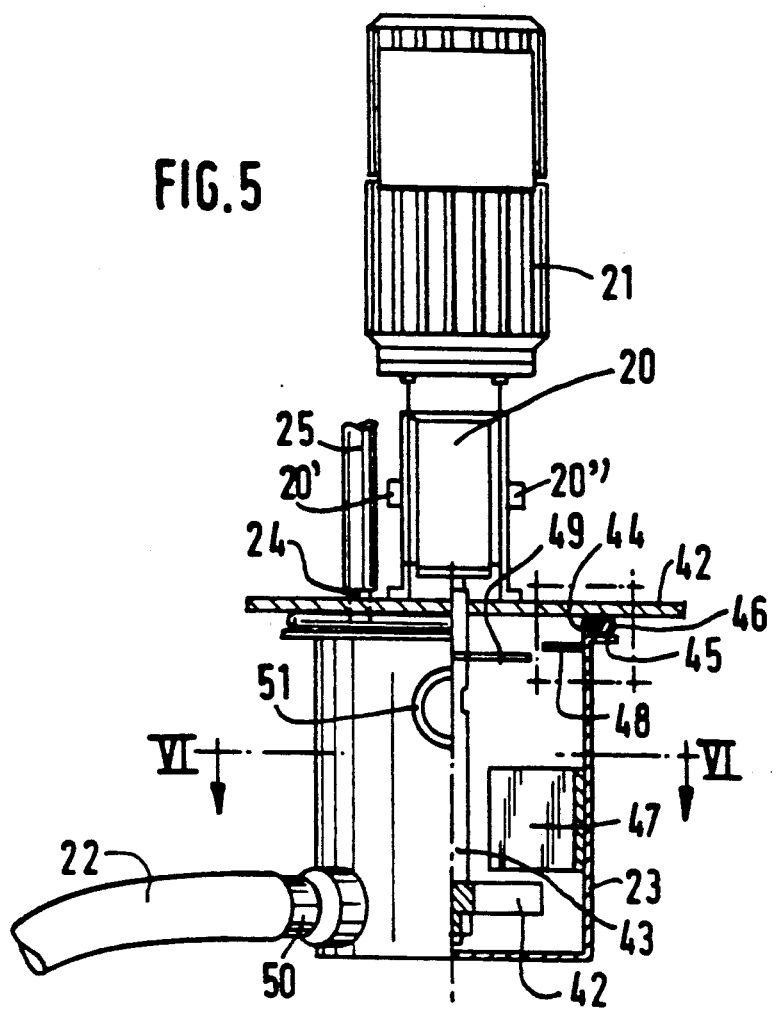
FIG. 5 is a schematic elevational view in partial cross-section, and on a larger scale, of a degassing portion of the device illustrated in FIG. 3.
Figure 6:
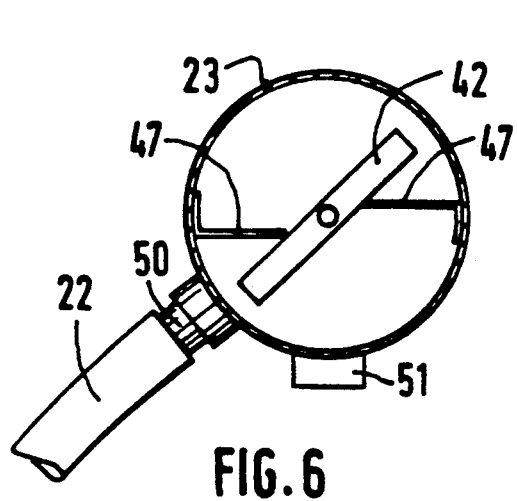
FIG. 6 is a cross-sectional view along lines VI—VI of FIG. 5.

A pair of radial deflectors 47, best seen in FIGS. 5 and 6, are positioned opposite to each other inside the container of the degassing device 23 and spaced vertically above the rotating agitator bar 42. The radial deflectors 47 help to accelerate degassing of the liquid while preventing the liquid from rotating inside the degassing device 23. A flange or ring 48 is located on the inside of the upper portion 44 of the container of the degassing device. This ring 48 defines a circular opening, a horizontal rotating disk 49 being connected to the output shaft 43 below the circular opening. The diameter of the rotating disk 49 is at least equal to the diameter of the circular opening defined by the ring or flange 48.

The container of the degassing device 23 has a liquid feed nozzle 50 disposed on a lower portion of the outside of the container. The flexible tube 22 from the pump 19 is connected to the feed nozzle 50. A nozzle 51 operates as an overflow device for removing the degassed liquid into a collecting basin (not shown). The nozzle 51 is mounted on the wall of the container of the degassing device 23 at a point below the rotating disk 49. FIG. 6 clearly shows the position of the nozzle 51 on the container of the degassing device, as well as nozzle 50, deflectors 47 and the rotating bar 42.

Figure 8:
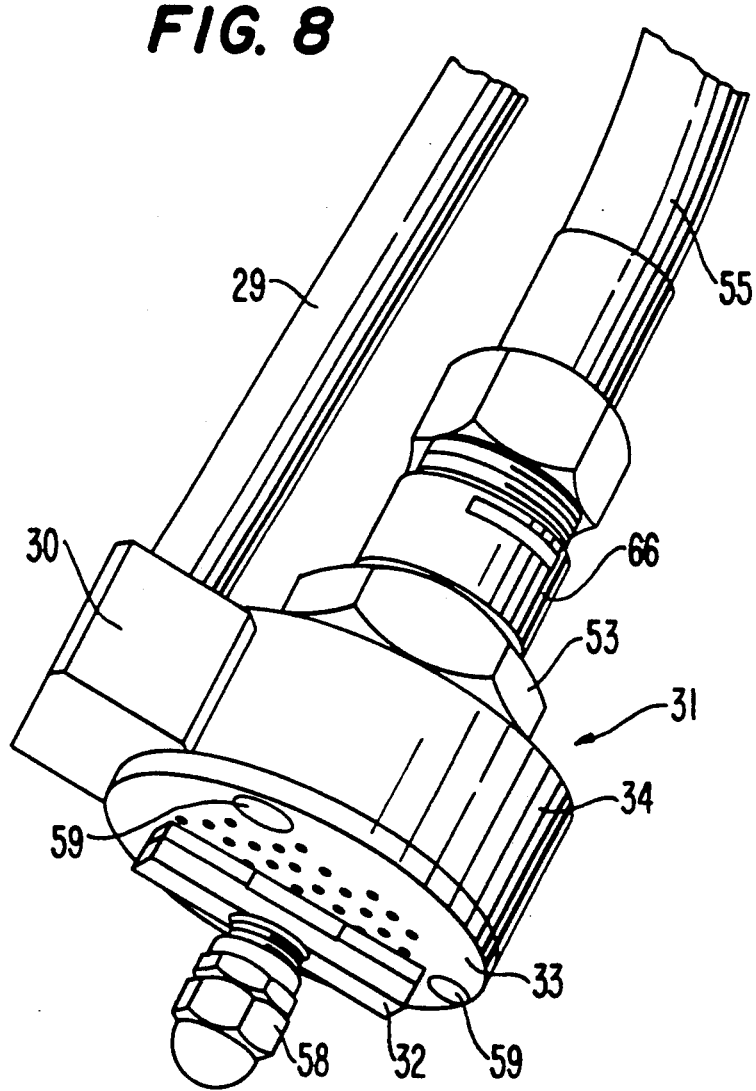
FIG. 8 is a schematic perspective view of a mud strainer according to the present invention.
Figure 9:
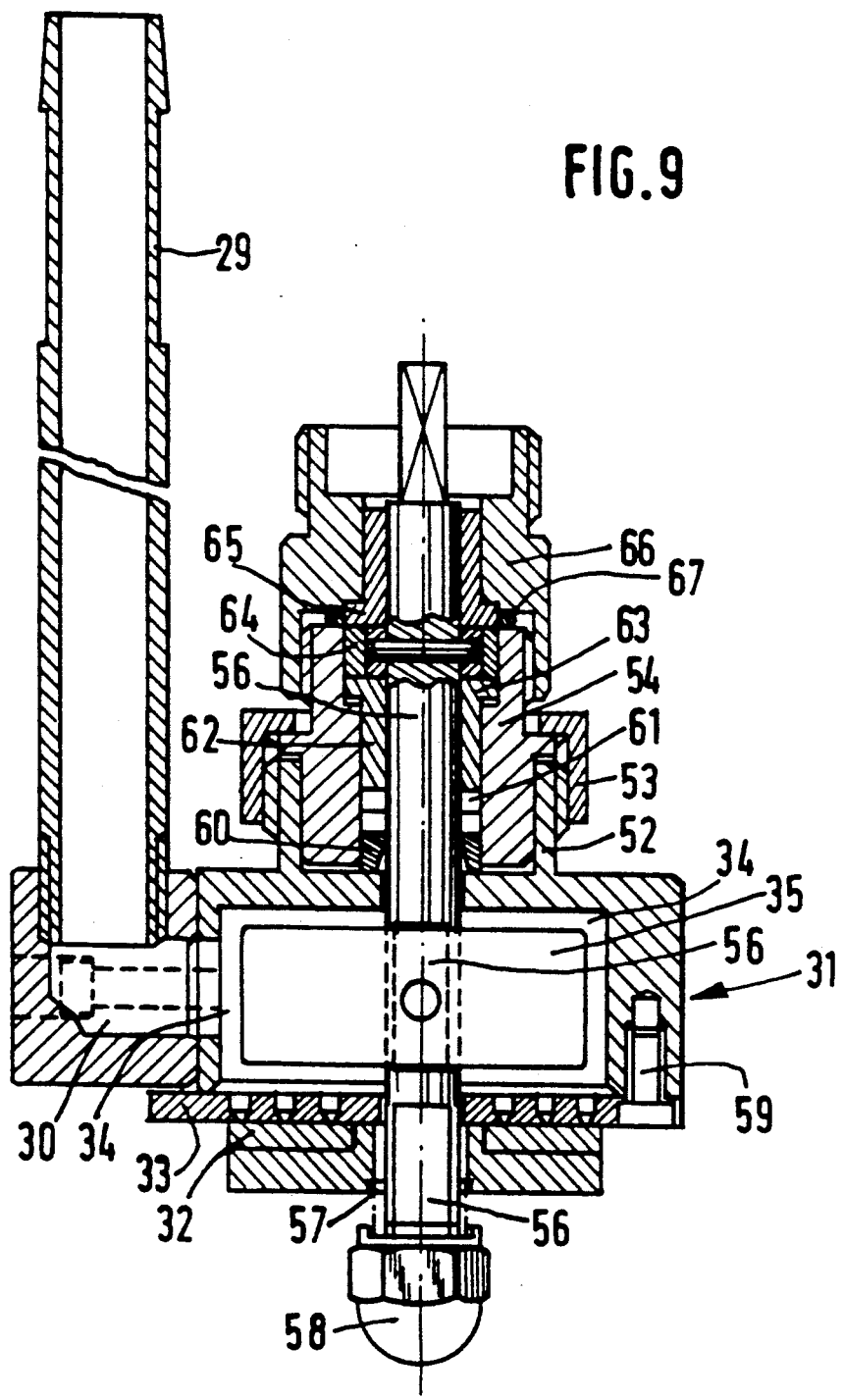
FIG. 9 is an enlarged cross-sectional view of the mud strainer of FIG. 8.

The strainer 31 is more clearly shown in FIGS. 8 and 9. Noting these Figures, the strainer has a cylindrical shape with a threaded collar 52 (see FIG. 9). A threaded sleeve 53 screws onto the threaded collar 52, the threaded sleeve shaped as a hexagonal nut and having a flange engaging a shoulder of a sleeve 54. The sleeve 54 is, in turn, supported on a body portion of the strainer 31 and serves to guide a rotary shaft 56.

Rotary shaft 56 is connected to a bowden wire housed in a casing 55. The casing 55 of the bowden wire extends to output 20" of the reducing gear 20, whereby the bowden wire and the rotating shaft 56 are driven by the motor 21 simultaneously with the pump 19 and the rotating bar 42 of the degassing device 23.

An arrangement is provided for agitating the liquid in the strainer housing to prevent encrustations inside the strainer 31. Preferably, a radial agitating blade 35 is rotatably mounted in a chamber 34 of the body of the strainer 31. Rotation of the radial agitating blade 35 thus prevents encrustations from forming on the inner wall of the body.

The inlet of the chamber 34 of the strainer 31 is closed by a perforated strainer plate or disk 33, which disk performs the actual straining function. A rotating scraper 32 is connected to the shaft 56 for rotary movement therewith. The rotating scraper 32 sweeps and cleans the outside surface of the perforated strainer disk 33. Preferably, the perforated disk and at least a portion of the rotating scraper are made of the same material. More preferably, the rotating scraper 32 and the perforated disk 33 are made of a material having a hardness sufficient, as measured on the Mohs scale, to withstand abrasion caused by the hardest minerals found in the liquid laden with solid particles. When used at an oil exploration site, the material should have a hardness sufficient to withstand abrasion caused by the hardest minerals in suspension in the drilling mud, for example tungsten carbide. Preferably, the rotating disk 32 is biased against the perforated disk 33. The arrangement for biasing the rotating scraper may take the form of a spring of the shaft 56 disposed between the rotating scraper and a capped nut 58 on end of the shaft 56.

The perforated disk 33, performing the actual straining function, is fastened onto the front or open side of the strainer body with screws 59. The chamber 34 of the strainer body is sealed at rotating shaft 56 with a presser member 60 fitted over the shaft and located at the bottom portion of the sleeve 54. A packing box 61 is clamped by a sleeve 62, the sleeve 62 having a collar 63 supported on a shoulder of the sleeve 54. The opposite side of collar 63 presses against a brace 64. The brace 64 is supported on its opposite side by a collar 65 of a ring member. The ring member is pressed against the brace 64 by a threaded sleeve 66, which is screwed onto a threaded portion of the sleeve 54. An annular seal 67 is interposed between the threaded sleeve 66 and the sleeve 64.

Figure 10:
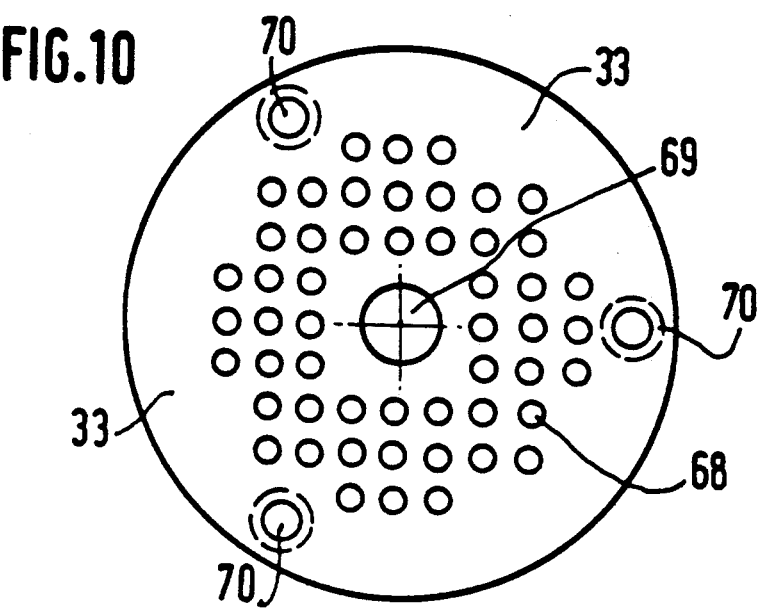
FIG. 10 is a schematic plan view of a strainer disk of the mud strainer of FIGS. 8 and 9.
Figure 11:
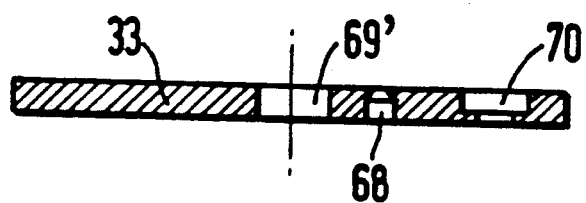
FIG. 11 is a diametral cross-sectional view of the strainer disk of FIG. 10.

Again referring to the perforated disk 33, FIG. 10 shows the disk as having a plurality of perforations 68 therethrough. In a preferred form of the invention, 52 perforations are distributed as evenly as possible about a central bore 69 of the perforated disk 33. The rotating shaft 56 passes through the central bore 69. Countersunk bores 70 are disposed about the periphery of the perforated disk for attaching the disk to the strainer body 34 with the screws 59. These bores 70 may be drilled through the perforated disk 33. Noting FIG. 11, the holes or perforations 68 of the perforated disk 33 are preferably formed so as to become progressively enlarged conically as the perforations 68 extend inwardly in the direction of the strainer chamber.

The above described perforations of the strainer plate, in combination with the rotating scraper 32, enable the prevention of oversize debris or rock fragments from penetrating the chamber 34 and the cavity 30. This will prevent damage to the pump 19, wherein the liquid, or in the case of an oil exploration site, drilling mud, must be as homogenous as possible when fed to the pump 19. A further preferred feature of the embodiment of the invention is that the minimum diameter of a single conical perforation of the perforated disk 33 is at most one millimeter.

Preferably, the pump 19 is a constant flow pump for providing a constant flow of liquid (or drilling mud) to the degassing device 23. More preferably, the constant flow pump is a peristaltic pump. Specifically, the constant flow pump has a flexible arc shaped tube which is progressively collapsed by the passage of a pad roller thereon. The pad roller may turn around a disk which supports the arc shaped tube on its edge. An example of this kind of pump is one manufactured by the Delasco Company. The gases released by the degassing device are extracted by a further suitable pumping device, which is not shown.

The above described apparatus according to the teachings of the present invention, working continuously, makes it possible to obtain a constant flow of liquid for sampling. This constant flow cannot become degassed before reaching the degassing device since the liquid is drawn from its source, in the case of oil exploration the source being the well head, and is conveyed directly without atmospheric contact to the degassing device 23. In the case of oil exploration, this apparatus thus gives an exact qualitative and quantitative indication of the hydrocarbons that are to be found at the various drilling levels. Furthermore, because of the continuous and accurate sampling performed, an adequate sampling of hydrocarbons can be obtained from the mud, giving the apparatus a high sensitivity.

Advantageously, the pump 19 will maintain the flow of mud at a constant value, preferably one and a half liters per minute. The suction flow of the gaseous mixture which is collected is approximately one half liter per minute, giving a ratio of three to one. All of the gaseous elements contained in the drilling mud are actually light hydrocarbons ranging from methane to normal pentane. These hydrocarbons are extracted at a rate of at least 85 to 90%, whatever the type and density of the drilling mud transporting the hydrocarbons to the surface. This is still true even if the drilling mud has a solvent base, such as gas oil, fuel oil or crude oil.

The following ratio exists between the gas contents measured by chromatography and the actual gas content of the mud:

$$\frac{\text{percentage of each constituent in the gas}}{\text{percentage of each constituent in the mud}} = \frac{\text{mud flow rate}}{\text{gas flow rate}} = \frac{1.5}{0.5} = 3$$

Although the method and apparatus of the present invention have been described and illustrated with respect to preferred features thereof, it is to be understood that various modifications and changes may be made to the specifically described and illustrated features without departing from the scope of the present invention. For example, the support frame of the apparatus could easily be modified from the frame shown. Similarly, the method of attaching the strainer could be modified. Volumes and flow rates may be mutually adjusted in order to insure the degassing of the liquid, while maintaining a constant ratio. Furthermore, in order to reduce the manufacturing costs of the rotating scraper 32, the scraper could be fitted with similar components made tungsten.

We claim:

1. An apparatus for sampling the gaseous content of a liquid laden with solids, comprising:
   a support frame;
   a degassing device mounted on said support frame for degassing sample liquid received therein to obtain a sample of gas of the sample liquid, said degassing device comprising a degassing container having an inlet connection for receiving sample liquid therethrough, a rotary degassing agitator, a discharge nozzle for discharging degassed sample liquid, and means for conducting sample gas from said degassing device for delivery to an analyzing device; and means for collecting sample liquid from a stream of the liquid and delivering substantially all of the sample liquid to said degassing container, said means for collecting and delivering comprising a pump mounted on said support frame having an input connection and an output connection, a flexible suction tube connected to said input connection, and a motor means mounted on said support frame for driving said pump, said output connection being fluidly connected to said inlet connection of said degassing container, and said rotary degassing agitator being driven by said motor means driving said pump.

2. The apparatus as set forth in claim 1, wherein said support frame comprises a support plate and a plurality of support legs connected thereto, said degassing container being connected to the underside of said support plate.

3. The apparatus as set forth in claim 2, wherein:
said degassing container is removably mounted on the underside of said support plate; and
said degassing container has a peripheral collar thereon and an O-ring seal on said collar for sealing contact with said support plate.

4. The apparatus as set forth in claim 2, wherein said motor means comprises a motor mounted on the top side of said support plate.

5. The apparatus as set forth in claim 1, wherein said means for collecting and delivering further comprises:
a suction strainer device connected to a suction end of said flexible suction tube.

6. The apparatus as set forth in claim 5, wherein said suction strainer device comprises:
a hollow strainer housing connected to said flexible suction tube;
a strainer plate on a suction side of said hollow strainer housing; and
means for continuously scraping the exterior side of said strainer plate when said pump is operating to suction sample fluid through said hollow strainer housing and said flexible suction tube.

7. The apparatus as set forth in claim 6, wherein said means for continuously scraping comprises:
a rotating scraper rotatably mounted on the exterior of said strainer plate; and
rotary driving means connected to said rotating scraper and drivably connected to said means for driving said pump.

8. The apparatus as set forth in claim 7, wherein:
said hollow strainer housing is cylindrical on the interior thereof;
said rotary driving means extends through said housing; and
a radial agitator blade is mounted on said rotary driving means in said strainer housing so as to rotate with said rotating scraper and agitate sample liquid in said housing.

9. The apparatus as set forth in claim 7, wherein:
said rotary driving means comprises a shaft extending through said hollow strainer housing and connected to said rotating scraper, and a bowden wire connected between said shaft and said means for driving said pump.

10. The apparatus as set forth in claim 7, wherein a capped nut and a spring are disposed on the exterior of said hollow strainer housing for biasing said rotating scraper against said strainer plate.

11. The apparatus as set forth in claim 6, wherein:
said strainer plate and at least a portion of said means for continuously scraping are made of the same material, said material having a hardness sufficient, according to the Mohs scale, to resist abrasion by any solids in the sample liquid.

12. The apparatus as set forth in claim 11, wherein said material comprises tungsten carbide.

13. The apparatus as set forth in claim 1, wherein:
said means for conducting sample gas from said degassing device comprises a gas evacuation tube disposed on an upper portion of said degassing container for connection to an analyzing device.

14. The apparatus as set forth in claim 13, wherein:
a lateral portion of said degassing container has said discharge nozzle thereon.

15. The apparatus as set forth in claim 14, wherein:
said degassing container has two radial deflectors therein above said rotary degassing agitator, an inner collar defining a circular opening between said motor and said rotary degassing agitator, and a rotary disk above said radial deflectors rotatably mounted with said rotary degassing agitator;
said radial deflectors are disposed below said inner collar; and
said inner collar circular opening has a diameter at most equal to the diameter of said rotary disk.

16. An apparatus for sample the gaseous content of a liquid laden with solids, comprising:
a support frame;
a degassing device mounted on said support frame for degassing sample liquid received therein to obtain a sample of gas of the sample liquid, said degassing device comprising a degassing container having an inlet connection for receiving sample liquid therethrough, a rotary degassing agitator, a discharge nozzle for discharging degassed sample liquid, and means for conducting sample gas from said degassing device for delivery to an analyzing device; and
means for collecting sample liquid from a stream of the liquid and delivering substantially all of the liquid to said degassing container, said means for collecting and delivering comprising a pump mounted on said support frame having an input connection and an output connection, a flexible suction tube connected to said input connection, and a motor means mounted on said support frame for driving said pump, said output connection being fluidly connected to said inlet connection of said degassing container, and said flexible suction tube having a hollow strainer housing connected thereto, said hollow strainer housing having a strainer plate on a suction side thereof and a means for continuously scraping the exterior side of said strainer plate when said pump is operating to suction sample fluid through said hollow strainer housing and said flexible suction tube, said means for continuously scraping being driven by said motor means driving said pump.

17. The apparatus as set forth in claim 16, wherein said means for continuously scraping comprises:
a rotating scraper rotatably mounted on the exterior of said strainer plate; and rotary driving means connected to said rotating scraper and drivably connected to said motor means driving said pump.

18. The apparatus as set forth in claim 17, wherein:
said hollow strainer housing is cylindrical on the interior thereof;
said rotary driving means extends through said housing; and
a radial agitator blade is mounted on said rotary driving means in said strainer housing so as to rotate with said rotating scraper and agitate sample liquid in said housing.

19. The apparatus as set forth in claim 18, wherein:
said strainer plate and at least a portion of said means for continuously scraping are made of the same material, said material having a hardness sufficient, according to the Mohs scale, to resist abrasion by any solids in the sample liquid.

20. The apparatus as set forth in claim 19, wherein said material comprises tungsten carbide.

21. The apparatus as set forth in claim 20, wherein a capped nut and a spring are disposed on the exterior of said hollow strainer housing for biasing said rotating scraper against said strainer plate.

22. The apparatus as set forth in claim 21, wherein:
said rotary driving means comprises a shaft extending through said hollow strainer housing and connected to said rotating scraper, and a bowden wire connected between said shaft and said means for driving said pump.

* * * * *